United States Patent
Sances et al.

(10) Patent No.: US 11,039,610 B2
(45) Date of Patent: Jun. 22, 2021

(54) METHODS AND COMPOSITIONS FOR CRYOPRESERVATION OF ENDOTHELIAL CELLS

(71) Applicant: Cedars-Sinai Medical Center, Los Angeles, CA (US)

(72) Inventors: Samuel Sances, Santa Monica, CA (US); Gad Vatine, Los Angeles, CA (US); Brandon Shelley, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 385 days.

(21) Appl. No.: 15/838,223

(22) Filed: Dec. 11, 2017

(65) Prior Publication Data

US 2018/0168144 A1 Jun. 21, 2018

Related U.S. Application Data

(60) Provisional application No. 62/433,151, filed on Dec. 12, 2016.

(51) Int. Cl.
  *A01N 1/02* (2006.01)
  *C12N 5/0797* (2010.01)
  *C12N 5/071* (2010.01)

(52) U.S. Cl.
  CPC ........... *A01N 1/0284* (2013.01); *C12N 5/069* (2013.01); *C12N 5/0623* (2013.01); *C12N 2506/45* (2013.01); *C12N 2523/00* (2013.01)

(58) Field of Classification Search
  None
  See application file for complete search history.

(56) References Cited

U.S. PATENT DOCUMENTS

2015/0017628 A1* 1/2015 Gibson ............... A01N 1/0221
  435/1.3

OTHER PUBLICATIONS

Patabendige et al., Brain Res. 1521: 16-30 (2013).*
Lippmann et al., Nat. Biotechnol. 30(8): 783-791 (2012).*
Wilson et al., Tissue Engineering: Part C 22(12): 1085-1094 (2016).*

* cited by examiner

*Primary Examiner* — Erin M. Bowers
(74) *Attorney, Agent, or Firm* — Nixon Peabody LLP; Linda B. Huber

(57) ABSTRACT

Brain microvascular endothelial cells (BMECS) can be generated from pluripotent stem cells, and possess membrane barrier functions along with capability for maturation into other developing tissues. This cell type has not been successfully frozen with loss of significant viability and/or BMEC functional properties. For example, BMECs can be used to model barrier function in blood brain barrier, by calculating the trans-endothelial resistance (TEER). However, thawed primary BMECs lose TEER resistance. By optimizing cell preparation, freezing media selection, and the controlled freezing, the Inventors have achieved complete recovery of frozen cells, achieving proper tight junction protein expression and physiologically relevant TEER. The freezing methods and compositions described herein, thereby allow for BMECs to be manufactured, frozen and distributed at scale.

22 Claims, 7 Drawing Sheets

Conditions: | Thaw Count/Viability
--- | ---
1. Hybernate Media (RT) | 3.4E5/60%
2. Hybernate Media (4°) | 4.0E5/40%
3. Cryostore Media (-195°) | 4.0E5/40%
4. Sigma Freezing Media (-195°) | 8.6E5/72%

Figure 6.
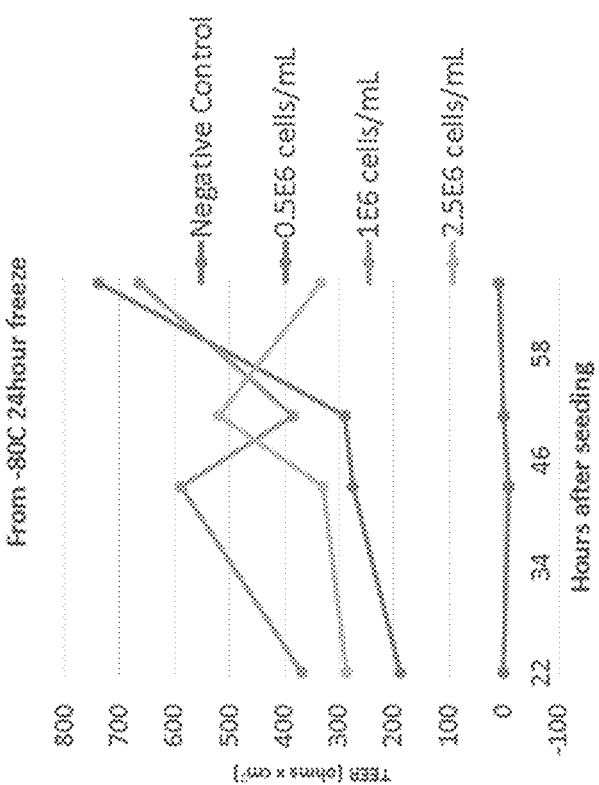
Fig. 6A
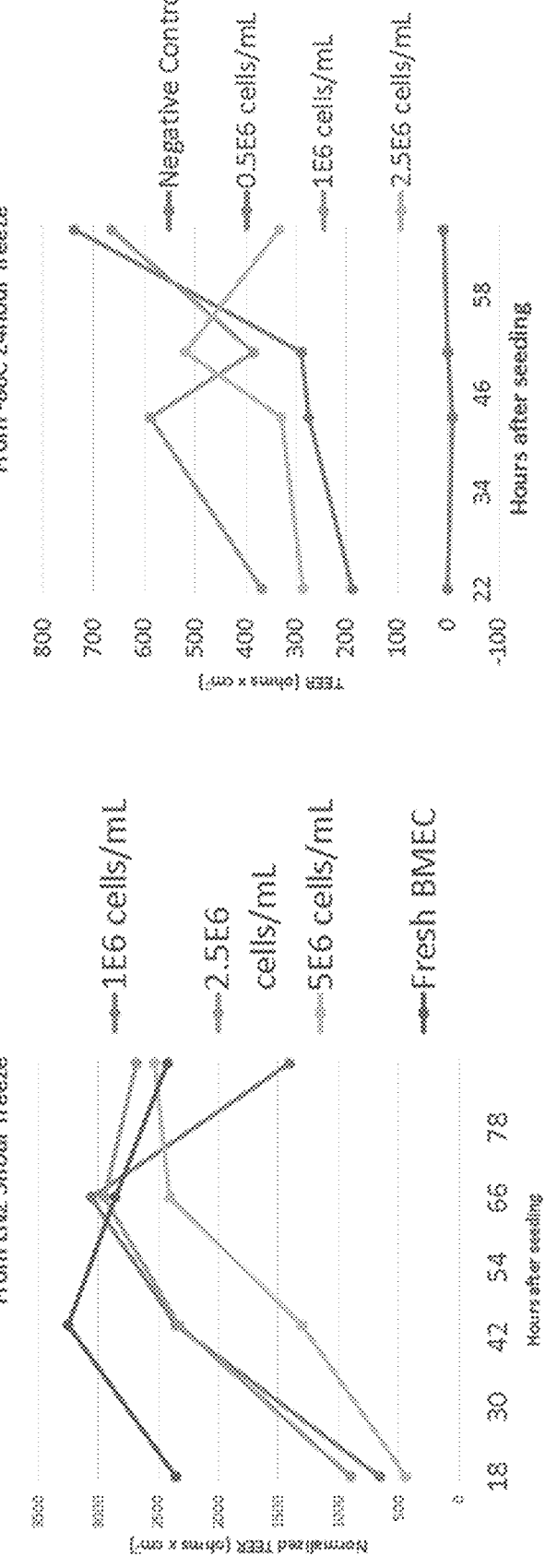
Fig. 6B

METHODS AND COMPOSITIONS FOR CRYOPRESERVATION OF ENDOTHELIAL CELLS

CROSS-REFERENCE TO RELATED APPLICATIONS

This application includes a claim of priority under 35 U.S.C. § 119(e) to U.S. provisional patent application No. 62/433,151 filed Dec. 12, 2016, the entirety of which is hereby incorporated by reference.

FIELD OF THE INVENTION

This invention relates to techniques and compositions for cryopreservation of endothelial cells.

BACKGROUND

The blood brain barrier (BBB) is of particular importance in the development of neurological drugs and related research. 95% of FDA approved molecules do not cross this barrier readily and current methods to test barrier permeability are lacking. Mouse models do not represent human barrier function and models commonly promote false positives. Human brain microvascular endothelial cells (BMECs), which constitute a layer of the BBB, are also hard to attain, and do not possess high resistance values when an immortalized cell line is used. The Inventors have devised techniques to generate large batches of iPSC-derived BMECs can be generated that carry ideal properties for drug discovery and other research. iPSC culture and differentiation to BMECs however, are not commonly available to researchers. Previous groups have not been able to attain fully functional iPSC-derived BMECs post-thawing. Others have used immortalized primary BMECs that are passaged over time post thaw. They possess less than a tenth of the trans-endothelial electrical resistance barrier function (TEER) necessary to properly model the BBB, and lack other physiologically relevant molecular and functional signatures of iPSC-derived BMECS. Thus, there is a great need in the art for techniques and compositions allowing for storage of BMECs, including iPSC-derived BMECs.

The Inventors have developed for the first time a method to cryogenically freeze large batches of iPSC-derived BMEC cells for use in an "on demand" format for many different research aims in medical research labs that are not equipped to generate the diversity of lines that can be distributed in frozen vials. Using novel method of filtration before freezing, optimum freezing media, and controlled rate freezing program, the Inventors have preserved functional properties of iPSC-derived BMEC cells post-thaw.

SUMMARY OF THE INVENTION

Described herein is a method of cryopreservation, including providing a quantity of brain microvascular endothelial cells (BMECs), suspending BMECs in a cryoprotective agent, exposing the BMECs to an initiation temperature, cooling the BMECs, supercooling the BMECs to a solid phase, heating the BMECs, and reducing the temperature of the BMEC solid phase. In other embodiments, the BMECs are filtered prior to suspension in the cryoprotective agent. In other embodiments, filtration includes extrusion of BMECs through a filter of about 20 to about 85 microns. In other embodiments, the BMECs are induced pluripotent stem cell (iPSC)-derived BMECs. In other embodiments, the cryoprotective agent includes serum. In other embodiments, the initiation temperature is about 2° to about 20° C. In other embodiments, the initiation temperature is about 3° to about 7° C. In other embodiments, cooling the BMECs includes reaching a temperature of about −3 to −7° C. In other embodiments, cooling the BMECs includes reaching a temperature of about −5° C. In other embodiments, supercooling the BMECs includes reaching a temperature of about −40 to −75° C. In other embodiments, supercooling the BMECs includes reaching a temperature of about −58° C. In other embodiments, supercooling is at a rate of about −45° C./minute. In other embodiments, heating the BMECs includes reaching a temperature of about −23° C. In other embodiments, heating the BMECs is at a rate of about +10° C./minute to about −26° C. and/or +3° C./minute to about −23° C. In other embodiments, reducing the temperature of the BMEC solid phase includes reaching a temperature of about −30° C. to about −50° C. In other embodiments, reducing the temperature of the BMEC solid phase includes reaching a temperature of about −40° C. In other embodiments, reducing the temperature of the BMEC solid phase is at a rate of about −0.8° C./minute. In other embodiments, rapid cooling of the reduced temperature BMEC solid phase at a rate of about −10° C./minute to about −100° C. and/or about −35° C./minute to about −160° C. In other embodiments, the method includes transfer of the BMECs to liquid nitrogen.

Also described herein is a frozen vial of iPSC-derived BMECs preserved by a method of cryopreservation, including providing a quantity of brain microvascular endothelial cells (BMECs), suspending BMECs in a cryoprotective agent, exposing the BMECs to an initiation temperature, cooling the BMECs, supercooling the BMECs to a solid phase, heating the BMECs, and reducing the temperature of the BMEC solid phase.

Also described herein is a method of cryopreservation, including providing a quantity of brain microvascular endothelial cells (BMECs), filtering the BMECs by extrusion of BMECs through a filter of about 20 to about 85 microns, suspending BMECs in a cryoprotective agent, exposing the BMECs to an initiation temperature to 3° to about 7° C., cooling the BMECs to the temperature of about −5° C., supercooling the BMECs at a rate of about −45° C./minute to a solid phase temperature of about −58° C., heating the BMECs at a rate of about +10° C./minute to about −26° C. and then +3° C./minute to about −23° C., and reducing the temperature of the BMEC solid phase at a rate of about −0.8° C./minute to about −40° C.

In other embodiments, the method includes rapid cooling of the reduced temperature BMEC solid phase at a rate of about −10° C./minute to about −100° C. and/or about −35° C./minute to about −160° C. In other embodiments, the method includes transfer of the BMECs to liquid nitrogen.

Further described herein is a frozen vial of iPSC-derived BMECs including cells with a trans-endothelial electrical resistance (TEER) value of about 1000-4000 ohms-cm$^2$.

BRIEF DESCRIPTION OF FIGURES

FIG. 6: Liquid nitrogen controlled rate freezing compared to conventional −80° C. freezing. (FIG. 6A) 83iCTR BMEC plated fresh (positive control) or frozen in liquid nitrogen (LN), then thawed same day. Thawed cells plated at different densities in ECM. (FIG. 6B) −80 freezing was also tested, and did not result in good TEER.

DETAILED DESCRIPTION

Figure 1:
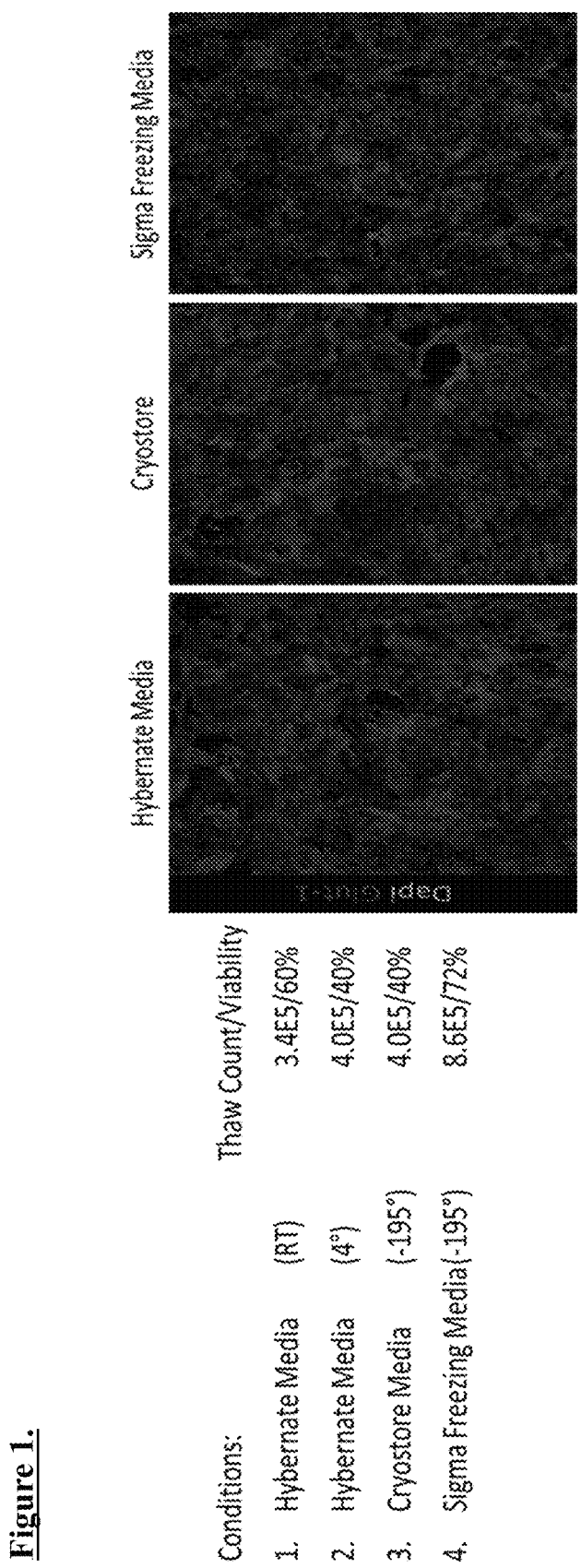
FIG. 1: Testing different freezing media. Sigma freezing media achieved critical viability for function post thaw. BMECs were differentiated and tested in different commercially available storage media for potential distribution. Cells were either stored at 4 degrees or frozen to −195° C. using the freezing protocol described herein. Cells were also plated and stained after 48 hours for BMEC marker glucose transporter 1 (GLUT-1). While Cryostore contained holes in the cell monolayer, Sigma Freezing Media had high viability post thaw and contained no holes.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The Inventors have previously described development of brain microvascular endothelial cells (BMECs) and applications in microfluidic devices for blood brain barrier (BBB) modeling, including as described in U.S. App. No. 62/243, 642, 62/277,723, 62/332,727, and 62/380,780, which are fully incorporated by reference herein. The Inventors have previously developed cryopreservation techniques for iPSCs and cells differentiated thereof, including for example, human neural progenitor cells described in Shelley et al., "A cGMP-applicable Expansion Method for Aggregates of Human Neural Stem and Progenitor Cells Derived From Pluripotent Stem Cells or Fetal Brain Tissue." *Journal of Visualized Experiments* 15:88 (2014), which is fully incorporated by reference herein. Techniques to a mass large numbers of cells for research experiments and clinical trials would greatly benefit the stem cell community, this includes batch production and freezing techniques for long-term storage and distribution. The Inventors are unaware of any success, however of the freezing of BMEC cells. Below describes a detailed protocol for the preparation, freezing and thawing of BMECs for use in BBB and organ-on-chip cultures.

The protocol for BMEC was developed de novo using basic principles required for efficient cryopreservation of mammalian cells and adapted for use in induced pluripotent stem cell (iPSC)-derived brain microvascular endothelial cell (BMEC) cryopreservation at an early stage. These cells contain human genetic material and have been shown to possess vascular barrier physiology that are similar to human brain vasculature.

BMECS can be generated from iPSCs, possess membrane barrier functions and provide maturation into other developing tissues. Barrier function in BBBs is quantified by calculating the trans-endothelial resistance (TEER). The human brain microvasculature has been measured to be anywhere from 1000-4000 ohms-cm$^2$ which the Inventors have achieved using iPSC-derived BMECs. So far, this cell type has not been successfully frozen and thawed to retain these barrier properties. However, by optimizing cell preparation, freezing media selection, and the controlled freezing, the Inventors have achieved complete recovery of frozen cells, achieving proper tight junction protein expression and TEER values of above 3000 ohms-cm$^2$ and up to 5000, achieved using a transwell system post-thaw. These cells can also be manufactured and frozen at scale.

The techniques and compositions described herein allows distribution of a notoriously difficult cell type to acquire due to poor function from primary human tissue origin. It has direct application for use in the research community that develops blood brain barrier (BBB) in vitro models for central nervous system drug discovery.

A variety of factors are known to influence cell survival during cryopreservation. It is generally assumed that conventional culture media used to nurture cells at physiological temperatures will also provide a suitable medium for exposure at low temperatures. However, it is now well established in tissue and organ preservation that the ionic and hydraulic balance in cells during hypothermia can be better controlled by using solutions designed to physically restrict temperature-induced imbalances. Cryoprotective agents are adapted for this purpose, whether intracellular cryoprotectants with low molecular weights that permeate cells for use in slow cooling, or high molecular weight composition that do not penetrate but maintain cell membrane integrity by direct protection in rapid cooling settings. In any case, preservation by cooling is achieved by striking a balance between the beneficial and harmful effects of reducing temperature. The most beneficial effect of cooling is the slowing of chemical reactions and, therefore, the decreased demand for oxygen and other substrates and the conservation of chemical energy. Rapid cooling may be harmful due to thermal shock. While common practice utilizes tissue culture media as the base solution for preservation media, such culture media are designed to maintain cellular function at normal physiological temperatures, and generally unsuitable for optimum preservation at reduced temperatures. In this aspect, different commercially available cryoprotective agents were tested.

In addition, cooling rate is known to have a most significant influence on cell survival. Controlled rate freezing before long-term storage maximizes viability for a wide variety of cells, rather than simply placing cells in a cooling environment. Cooling samples to their freezing point and beyond does not automatically result in freezing the samples at the equilibrium freezing point. Invariably, samples tend to under cool, often referred to as supercooling, depending on cooling rate, sample size, and presence of nucleating agents, which are foreign particles in solution that catalyze the formation of an ice nucleus, initiating the freezing process.

Controlling nucleation and the temperature compensation provided during controlled rate preservation for release of the latent heat of fusion results in improved post-freeze cell viability. This is a major reason to use controlled rate freezing equipment rather than simply to place samples in cold environments. The controlled rate freezing equipment chamber design eliminates variable degrees of supercooling by a programmed decrease in chamber temperature that both initiates nucleation and subsequently compensates for the release of the latent heat of fusion. The major variables involved are rate of chamber temperature decrease, hold temperature and duration, the rate of temperature increase, and the temperature at which chamber cooling is re-initiated.

Described herein is a method of cryopreservation, including providing a quantity of brain microvascular endothelial cells (BMECs), suspending BMECs in a cryoprotective agent, exposing the BMECs to an initiation temperature, cooling the BMECs, supercooling the BMECs to a solid phase, heating the BMECs, and reducing the temperature of the BMEC solid phase. In other embodiments, the BMECs are filtered prior to suspension in the cryoprotective agent. In other embodiments, filtration includes extrusion of BMECs through a filter of about 10 to about 125 microns. In other embodiments, filtration includes extrusion of BMECs through a filter of about 20 to about 85 microns. In other embodiments, the BMECs are induced pluripotent stem cell (iPSC)-derived BMECs. In other embodiments, the cryoprotective agent includes serum. In other embodiments, the initiation temperature is about −4° to about 40° C. In other embodiments, the initiation temperature is about 2° to about 20° C. In other embodiments, the initiation temperature is about −1° to about 15° C. In other embodiments, the initiation temperature is about 3° to about 7° C. In other embodiments, cooling the BMECs includes reaching a temperature of about −5 to −15° C. In other embodiments, cooling the BMECs includes reaching a temperature of about −3 to −7° C. In other embodiments, cooling the BMECs includes reaching a temperature of about −5° C. In other embodiments, supercooling the BMECs includes reaching a temperature of about −20 to −90° C. In other embodiments, supercooling the BMECs includes reaching a temperature of about −40 to −75° C. In other embodiments, supercooling the BMECs includes reaching a temperature of about −58° C. In other embodiments, supercooling is at a rate of about −20 TO −60° C./minute. In other embodiments, supercooling is at a rate of about −45° C./minute. In other embodiments, heating the BMECs includes reaching a temperature of about −23° C. In other embodiments, heating the BMECs is at a rate of about +10° C./minute to about −26° C. and/or +3° C./minute to about −23° C. In other embodiments, reducing the temperature of the BMEC solid phase includes reaching a temperature of about −30° C. to about −50° C. In other embodiments, reducing the temperature of the BMEC solid phase includes reaching a temperature of about −40° C. In other embodiments, reducing the temperature of the BMEC solid phase is at a rate of about −3 to −0.05° C./minute. In other embodiments, reducing the temperature of the BMEC solid phase is at a rate of about −0.8° C./minute. In other embodiments, rapid cooling of the reduced temperature BMEC solid phase at a rate of about −10° C./minute to about −100° C. and/or about −35° C./minute to about −160° C. In other embodiments, the method includes transfer of the BMECs to liquid nitrogen.

Also described herein is a frozen vial of iPSC-derived BMECs preserved by a method of cryopreservation, including providing a quantity of brain microvascular endothelial cells (BMECs), suspending BMECs in a cryoprotective agent, exposing the BMECs to an initiation temperature, cooling the BMECs, supercooling the BMECs to a solid phase, heating the BMECs, and reducing the temperature of the BMEC solid phase.

Also described herein is a method of cryopreservation, including providing a quantity of brain microvascular endothelial cells (BMECs), filtering the BMECs by extrusion of BMECs through a filter of about 20 to about 85 microns, suspending BMECs in a cryoprotective agent, exposing the BMECs to an initiation temperature to 3° to about 7° C., cooling the BMECs to the temperature of about −5° C., supercooling the BMECs at a rate of about −45° C./minute to a solid phase temperature of about −58° C., heating the BMECs at a rate of about +10° C./minute to about −26° C. and then +3° C./minute to about −23° C., and reducing the temperature of the BMEC solid phase at a rate of about −0.8° C./minute to about −40° C.

In other embodiments, the method includes rapid cooling of the reduced temperature BMEC solid phase at a rate of about −10° C./minute to about −100° C. and/or about −35° C./minute to about −160° C. In other embodiments, the method includes transfer of the BMECs to liquid nitrogen.

Further described herein is a frozen vial of iPSC-derived BMECs including cells with a trans-endothelial electrical resistance (TEER) value of about 1000-4000 ohms-cm$^2$.

Example 1

Preparation of BMECs

Briefly, techniques for generation of iPSC-derived brain microvascular endothelial cells (BMECs) are described.

iPSCs are cultured at low density and for 8 days what follows is unique cell handling that allow for successful freezing of cells.

Upon BMEC generation, cells colonies are assessed for BMEC formation and quality. If the quality of the culture is acceptable, the cells are incubated in commercial enzyme accutase for 20-25 minutes. Cells are then washed off the plastic with a stereological pipette, diluted in cold phosphate buffer saline (PBS) and centrifuged.

Cells are then resuspended in cold PBS and ran through a 40-micron filter to remove clumps of neural tissue. Removal of neural tissue was observed as an important step in allowing for adequate TEER values post-thaw, potentially due to removal to extracellular nucleating agents that would damage cellular membrane.

Cells are quantified, spun down again, and resuspended in commercially available sigma freezing media. Different medias were tested originally and determined to have different viabilites upon thawing. Sigma freezing media contains serum which could account for its success opposed to others tested such as the industry standard Cryostore.

3 million cells are distributed in 500 uL of media per vial and frozen using the control rate freezer.

Example 2

BMEC Freezing Protocol

The use of a controlled rate freezer employs liquid nitrogen to be released as a gas in highly regulated spurts under constantly monitored temperatures of both the chamber of the freezer (chamber) as well as a temperature probe (probe) that has been inserted into a cryovial containing the media (no cells) used to cryopreserve the cells. The software employs both temperature probes for the application of steps in the protocol. One may write protocols using both the chamber temperature or probe temperature as triggers for the next step.

By adjusting the triggers and/or temperatures one can optimize the freezing process so as to create a protocol that is superior to standard static isopropyl alcohol methods as well as other standard controlled rate freezer protocols. The most critical aspects of the procedure involve the cooling rate for various steps. The cryopreservation of BMEC can be broken down into 5 important steps.

1. Initiation Temperature—The cells must be initiated at a temperature of 2-20° C. Once transferred to the chamber the temperature is held for five minutes in order to establish an equilibrium. Step 2 is triggered by a timer, neither the specific chamber nor probe temperature is required for this step.
2. Liquid Cooling Stage—The cells are then dropped from the chamber temperature of 4° C. to a probe temperature of −5° C. Standard controlled rate freezer protocols initiate step 3 upon a chamber temperature. This protocol however relies on the probe temperature of −5° C. This is critical to the process, which ensures that the samples reach −5° C. before the next step.
3. Supercooling/Phase Change Stage—When the sample probe reaches −5° C., the program requires a rapid temperature drop at a rate of −45° C./minute to −58° C. The rapid temperature drop creates a state where the liquid is supercooled as a liquid before turning into the solid phase. The rapid cooling of this step is important to minimize the temperature increase that occurs during the latent heat of fusion phase change i.e.; when the liquid turns into a solid (exothermic process). In order to stop the samples from freezing too quickly after the supercooling/heat of fusion event, the chamber temperature is brought back up via heating to −26° C. at a rate of +10° C./minute and then to −23° C. at a rate of +3° C./minute. The chamber temperature is used to trigger these steps.
4. Once the sold phase has been obtained it is important to drop the temperature of the samples at a rate of −0.8° C. until the temperature of −40° C. is reached. In order to ensure the samples have reached −40° C., the following step is triggered on the sample temperature as opposed to the chamber temperature. After the temperature of the samples has reached −40° C. the cells may be rapidly cooled at a rate of −10° C./minute to −100° C. and then to −160° C. at a rate of −35° C.
5. When the chamber temperature has reached −160° C., the cells may be transferred to liquid nitrogen gas phase long-term storage.

TABLE 1

BMEC Cryopreservation Steps

| Step | Rate (° C./min) | End Temp (° C.) | Hold (m s) | Triger |
|---|---|---|---|---|
| 1 | | | 5 m 0 s | Chamber |
| 2 | −1.30 | −5.00 | | Sample |
| 3 | | | 1 m 0 s | Chamber |
| 4 | −45.00 | −58.00 | | Chamber |
| 5 | +10.00 | −26.00 | | Chamber |
| 6 | +3.00 | −23.00 | | Chamber |
| 7 | −0.80 | −40.00 | | Sample |
| 8 | −10.00 | −100.00 | | Chamber |
| 9 | −35.00 | −160.00 | | Chamber |

Example 3

Thawing Protocol

BMECs can be thawed in standard fashion by 37° C. water bath. Cells are resuspended immediately in PBS and centrifuged. Cells are then resuspended in endothelial cell media (ECM).

Optimum seeding density was determined to be 1E6 with fresh cells as described in Shelley et al. 15:88 (2014), which is fully incorporated by reference herein.

Example 4

Results

Figure 2:
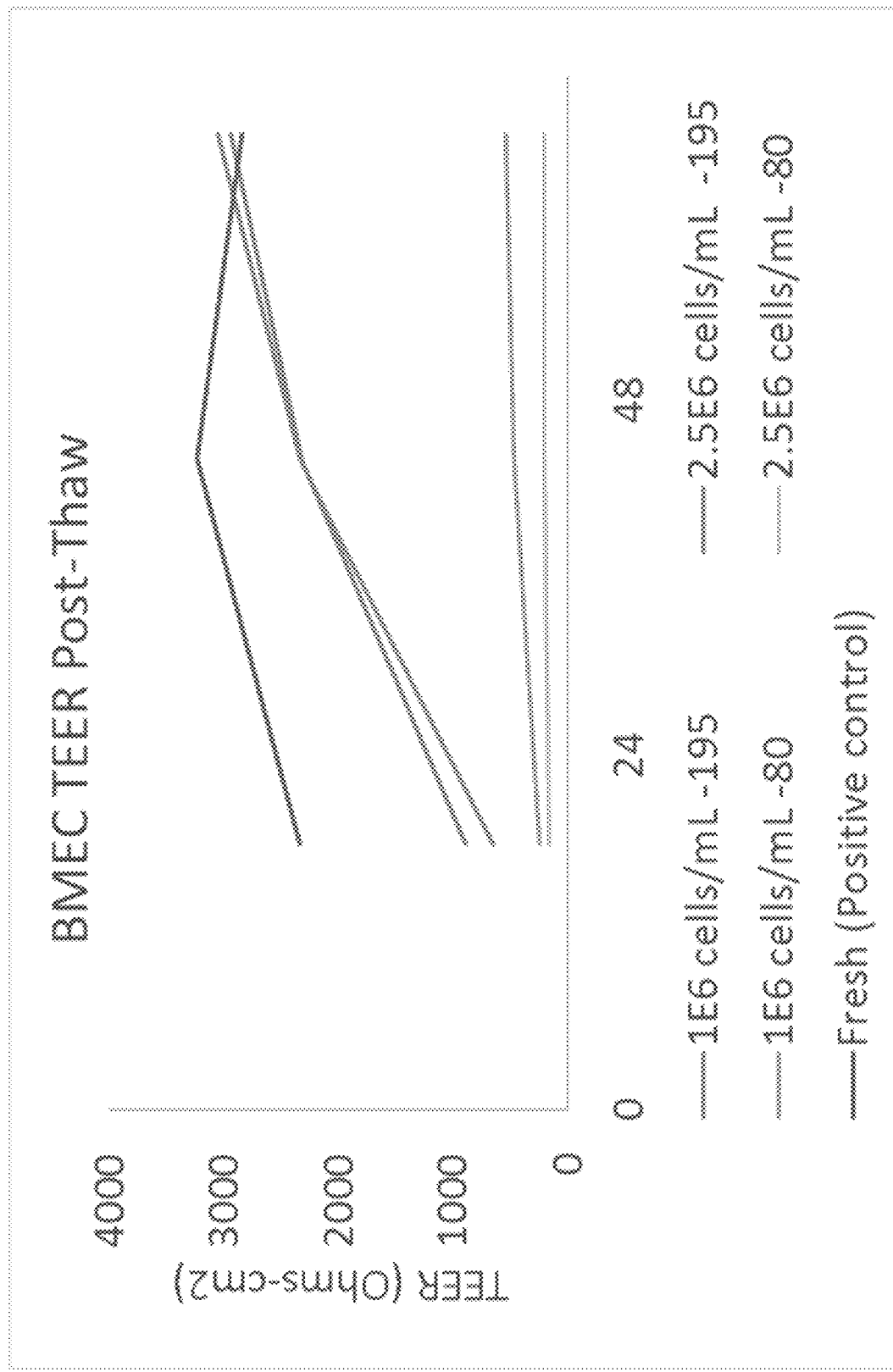
FIG. 2: Physiologically relevant TEER values were achieved in iPSC-derived cells that had previously been frozen for 2 weeks in liquid nitrogen. BMECs were either frozen in standard ethanol housing at −80° C., or through use of control rate freezer in liquid nitrogen. Previous attempts using standard ethanol housing directly to −195° C. were also unsuccessful. BMECs were then thawed and plated into transwell membrane cultures to test for membrane properties. Cells frozen by control rate freezer regained TEER after 48 hours.
Figure 3:
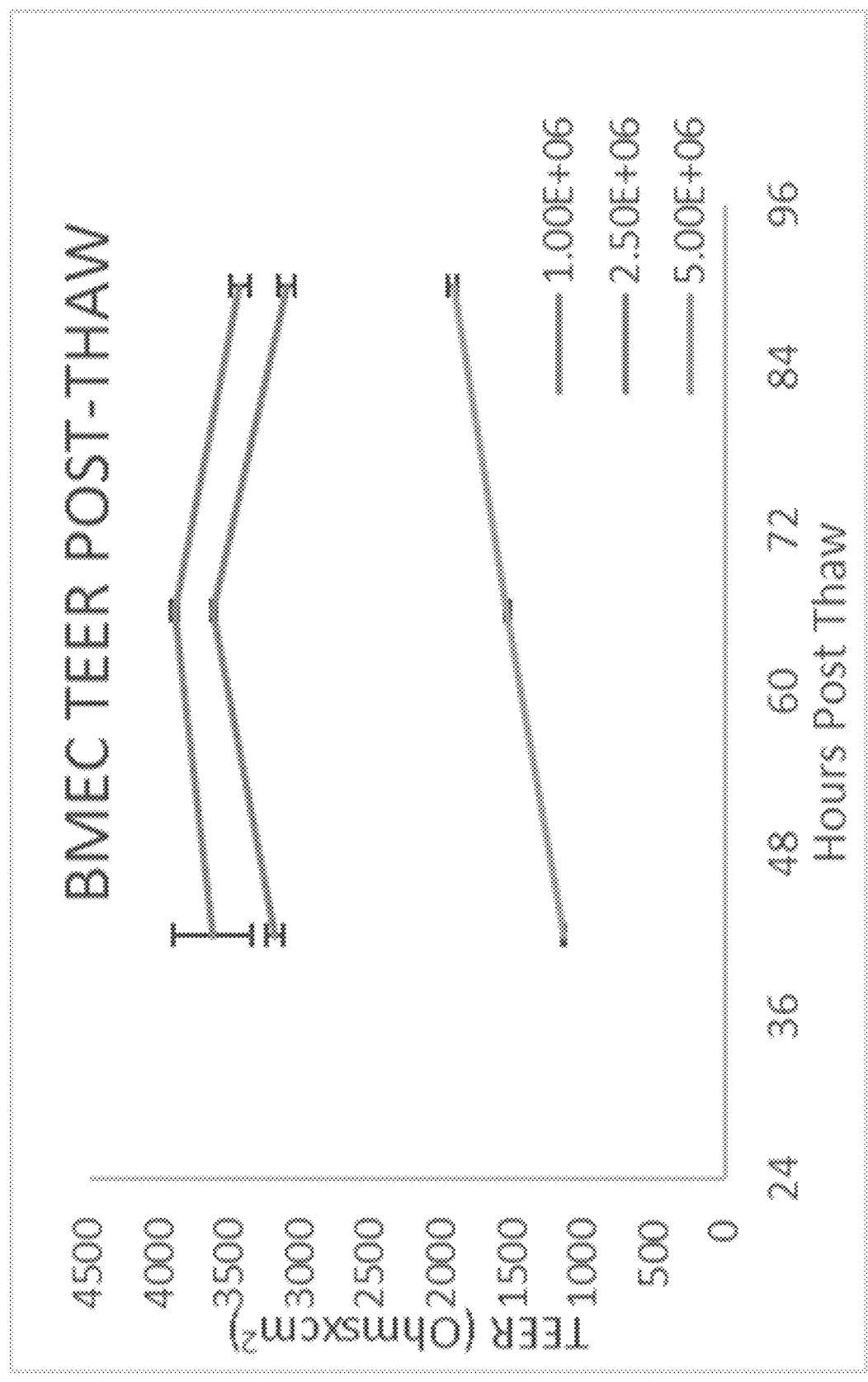
FIG. 3: Separate differentiation and freezing using same protocol repeated high TEER values. The same iPSC line was differentiated into biologically distinct cohort of BMECs and frozen using optimum conditions at different seeding densities in transwell membrane cultures. After freezing control rate freezer, and storing in liquid nitrogen (LN) for 1 week, cells were thawed at different densities per well, and TEER recorded starting after 42 hours. BMECs cultures retained excellent TEER function after 48 hours.
Figure 4:
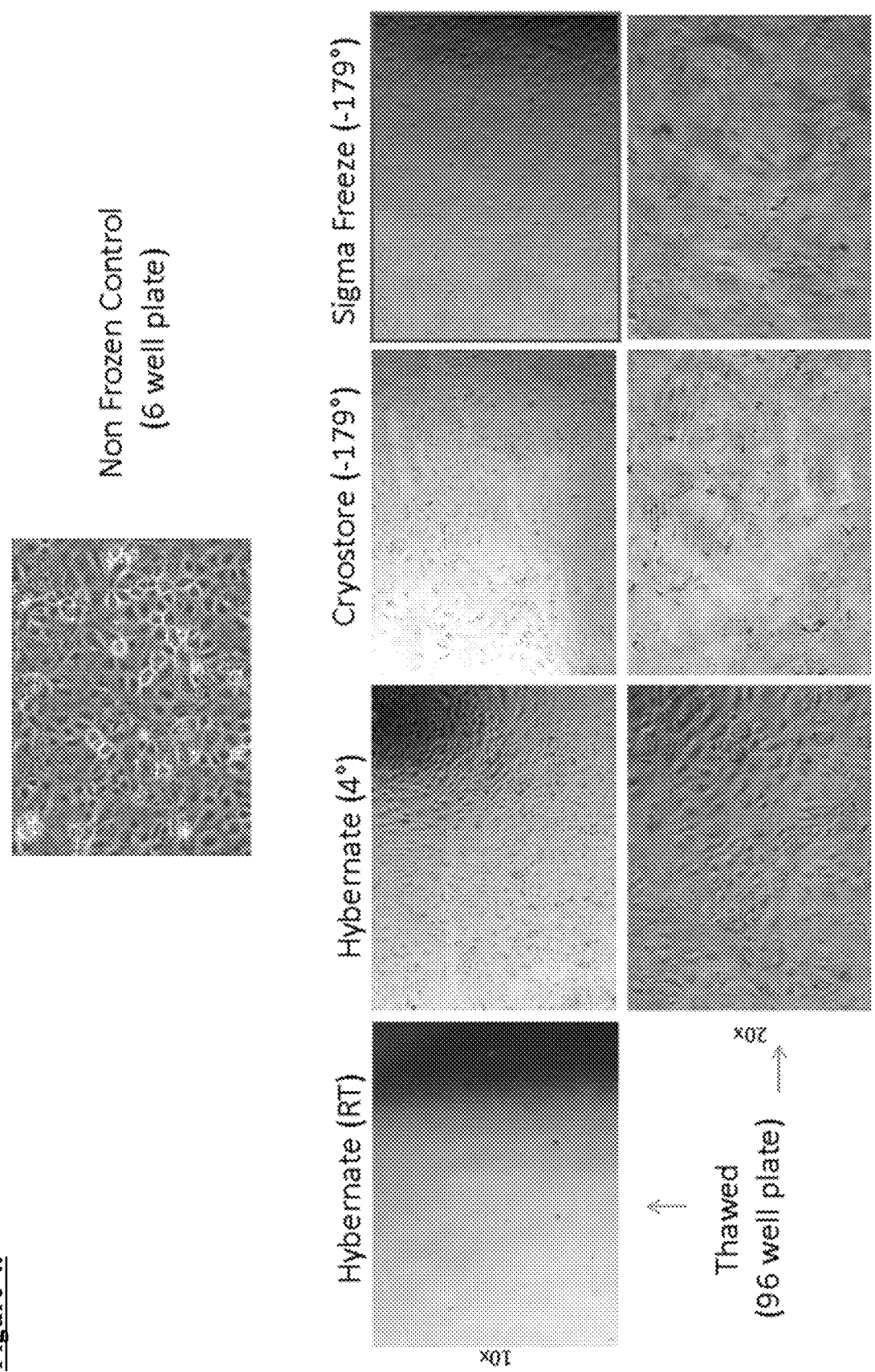
FIG. 4: Thawed iPSC-derived BMECs. 83iCTR33n1 iPSCs differentiated to BMECs and put in storage conditions at for viability testing 2 days BMEC progenitor differentiation. Cells thawed 3 days later and plated on collagen/fibronectin on 96 well format. Cells fixed and stained three days post thaw.
Figure 5:
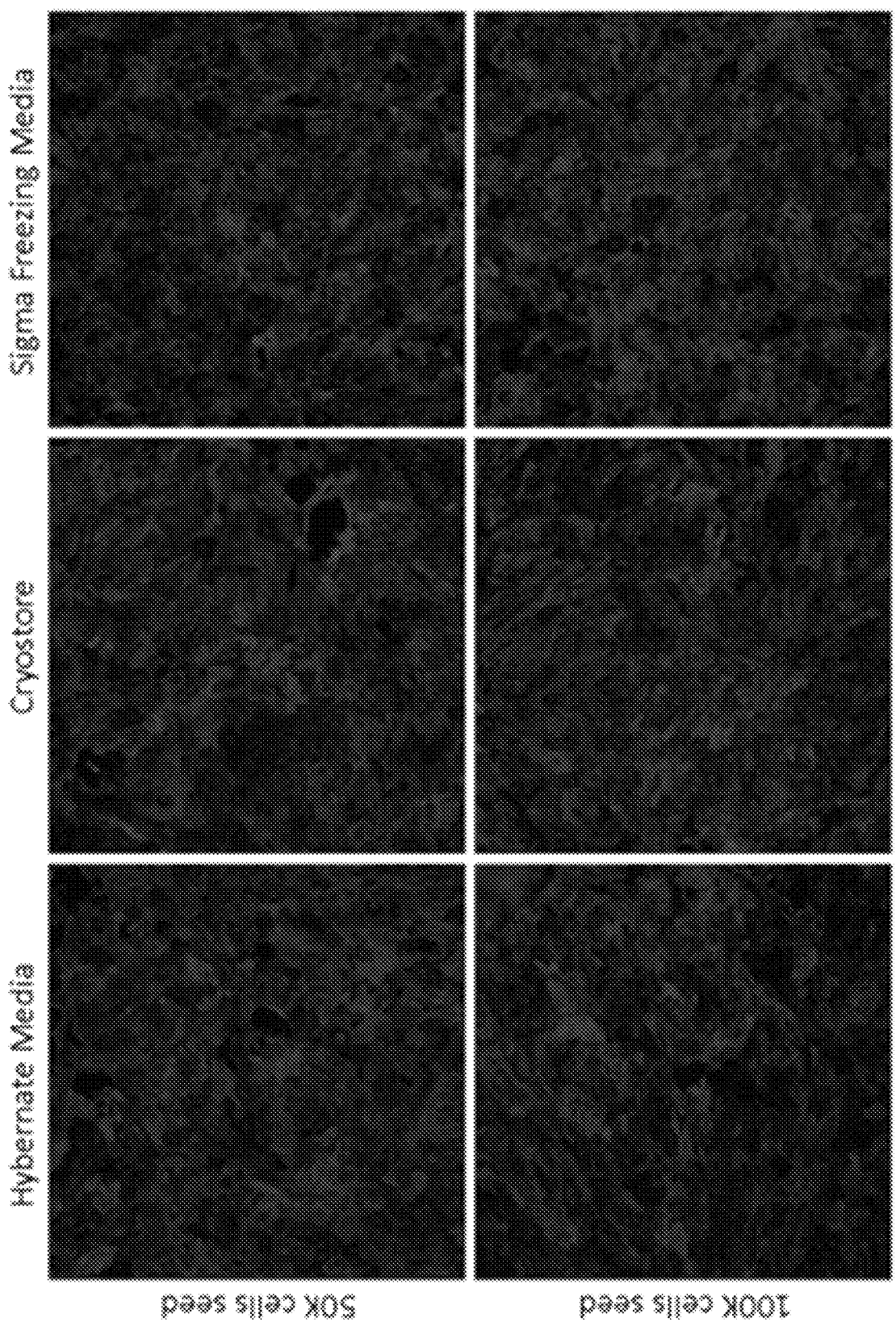
FIG. 5: Additional testing different freezing media and seeding densities. Cells were plated at 50K and 100K seeding densities and stained after 48 hours for BMEC marker glucose transporter 1 (GLUT-1).
Figure 7:
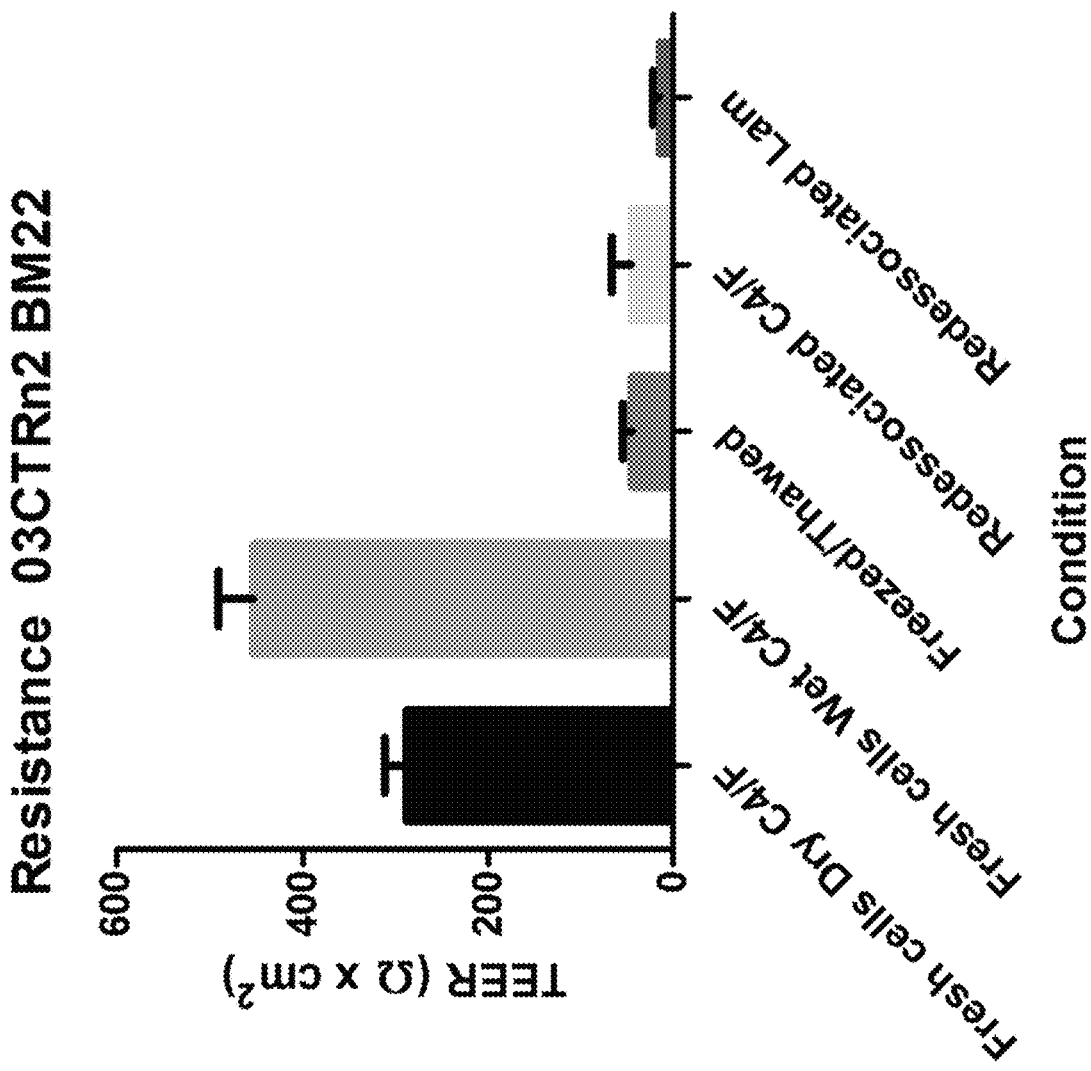
FIG. 7: Conventional freezing. An example of conventional freezing by placement in cold environment did not allow for preservation of functional TEER values suitable for use in BBB modeling.

As shown in FIG. 1, Sigma freezing media achieved critical viability for function post thaw, as demonstrated by high viability and integrity (e.g., no holes) of cellular monolayer, potentially due to the presence of serum in Sigma freezing media. As shown in FIGS. 2 and 3, BMECs could be frozen using the described protocols, then thawed and plated into transwell membrane cultures to test for membrane properties. Additional depictions are shown in FIGS. 4-6. Cells frozen by control rate freezer regained TEER after 48 hours compared to conventional freezing, which did not possess physiologically relevant TEER values as shown in FIG. 7.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are techniques and compositions for cryopreservation of brain microvascular endothelial cells (BMECs), including iPSC-derived BMECs, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of cryopreservation, comprising:
   (a) providing a quantity of brain microvascular endothelial cells (BMECs);
   (b) suspending BMECs in a cryoprotective agent;
   (c) exposing the BMECs to an initiation temperature;
   (d) cooling the BMECs;
   (e) supercooling the BMECs to generate a BMEC solid phase;
   (f) heating the BMEC solid phase without melting; and
   (g) reducing the temperature of the BMEC solid phase after heating the BMEC solid phase, wherein subsequent thawing of the BMEC solid phase produces thawed BMECs with a transepithelial electrical resistance (TEER) of over 3000 Ω·cm² about 48 hours after thawing.

2. The method of claim 1, wherein the BMECs are filtered prior to suspension in the cryoprotective agent.

3. The method of claim 2, wherein filtration comprises extrusion of BMECs through a filter of about 20 to about 85 microns.

4. The method of claim 1, wherein the BMECs are induced pluripotent stem cell (iPSC)-derived BMECs.

5. The method of claim 1, wherein the cryoprotective agent comprises serum.

6. The method of claim 1, wherein the initiation temperature is about 2° to about 20° C.

7. The method of claim 6, wherein the initiation temperature is about 3° to about 7° C.

8. The method of claim 1, wherein cooling the BMECs comprises reaching a temperature of about −3 to −7° C.

9. The method of claim 8, wherein cooling the BMECs comprises reaching a temperature of about −5° C.

10. The method of claim 1, wherein supercooling the BMECs comprises reaching a temperature of about −40 to −75° C.

11. The method of claim 10, wherein supercooling the BMECs comprises reaching a temperature of about −58° C.

12. The method of claim 1, wherein supercooling is at a rate of about −45° C./minute.

13. The method of claim 1, wherein heating the BMEC solid phase comprises reaching a temperature of about −23° C.

14. The method of claim 1, wherein heating the BMEC solid phase is at a rate of about +10° C./minute to about −26° C. and/or +3° C./minute to about −23° C.

15. The method of claim 1, wherein reducing the temperature of the BMEC solid phase comprises reaching a temperature of about −30° C. to about −50° C.

16. The method of claim 15, wherein reducing the temperature of the BMEC solid phase comprises reaching a temperature of about −40° C.

17. The method of claim 1, wherein reducing the temperature of the BMEC solid phase is at a rate of about −0.8° C./minute.

18. The method of claim 1, further comprising rapid cooling of the reduced temperature BMEC solid phase at a rate of about −10° C./minute to about −100° C. and/or about −35° C./minute to about −160° C.

19. The method of claim 1, further comprising transfer of the BMECs to liquid nitrogen.

20. A method of cryopreservation, comprising:
(a) providing a quantity of brain microvascular endothelial cells (BMECs);
(b) filtering the BMECs by extrusion of BMECs through a filter of about 20 to about 85 microns;
(c) suspending BMECs in a cryoprotective agent;
(d) exposing the BMECs to an initiation temperature to 3° to about 7° C.;
(e) cooling the BMECs to the temperature of about −5° C.;
(f) supercooling the BMECs at a rate of about −45° C./minute to a solid phase temperature of about −58° C. to generate a BMEC solid phase;
(g) heating the BMEC solid phase without melting at a rate of about +10° C./minute to about −26° C. and then +3° C./minute to about −23° C.; and
(h) reducing the temperature of the BMEC solid phase at a rate of about −0.8° C./minute to about −40° C. after heating the BMEC solid phase to about −23° C., wherein subsequent thawing of the BMEC solid phase produces thawed BMECs with a transepithelial electrical resistance (TEER) of over 3000 Ω·cm² about 48 hours after thawing.

21. The method of claim 20, further comprising rapid cooling of the reduced temperature BMEC solid phase at a rate of about −10° C./minute to about −100° C. and/or about −35° C./minute to about −160° C.

22. The method of claim 20, further comprising transfer of the BMECs to liquid nitrogen.

\* \* \* \* \*